United States Patent [19]
Clark et al.

[11] Patent Number: 5,719,784
[45] Date of Patent: Feb. 17, 1998

[54] ORDER-BASED ANALYSES OF CELL AND TISSUE STRUCTURE

[75] Inventors: John I. Clark; Shahram Vaezy, both of Seattle, Wash.

[73] Assignee: University of Washington at Seattle, Seattle, Wash.

[21] Appl. No.: 446,696

[22] PCT Filed: Dec. 14, 1993

[86] PCT No.: PCT/US93/12149

§ 371 Date: Jun. 7, 1995

§ 102(e) Date: Jun. 7, 1995

[87] PCT Pub. No.: WO94/14063

PCT Pub. Date: Jun. 23, 1994

Related U.S. Application Data

[63] Continuation-in-part of Ser. No. 991,583, Dec. 14, 1992, abandoned.

[51] Int. Cl.⁶ .................. G01N 33/48; G01N 33/483; G06F 17/159
[52] U.S. Cl. .................................. 364/496; 382/133
[58] Field of Search ..................... 364/413.08, 413.1, 364/413.2, 496; 377/10; 382/133, 280

[56] References Cited

U.S. PATENT DOCUMENTS

| | | | |
|---|---|---|---|
| 3,315,229 | 4/1967 | Smithline | 377/10 X |
| 4,150,360 | 4/1979 | Kopp et al. | 382/133 |
| 4,213,036 | 7/1980 | Kopp et al. | 382/133 |
| 4,789,993 | 12/1988 | Chen et al. | 364/413.13 |
| 4,965,725 | 10/1990 | Rutenberg | 364/413.1 |
| 5,029,475 | 7/1991 | Kikuchi et al. | 73/602 |
| 5,073,857 | 12/1991 | Peters et al. | 364/413.1 |

OTHER PUBLICATIONS

Richard F. Voss, Fractals in Nature: From Characterization to Simulation, Science of Fractal Images (1988), Chapt. 1, pp. 21–70.

Shahram Vaezy, Fourier Analysis of Digital Stem Images in the Study of Transparency in Human Cornea and Sclera, Proceedings of the 46th Annual Meeting of the Electron Microscopy Society of America (1988), pp. 178–179.

Shahram Vaezy, John I. Clark and Judy M. Clark, Fourier Analysis of Two Structures in Opacifying House Lens, Proceedings of the XIIth Congress for Electron Microscopy (1990), pp. 554–555.

Shahram Vaezy and John I. Clark, A Quantitative Analysis of Transparency in the Human Sclera and Cornea Using Fourier Methods, Journal of Microscopy, Jul. 1991, vol. 163, Pt. 1, pp. 85–94.

Margo Gisselberg, John I. Clark, Shahram Vaezy and Thomas B. Osgood, A Quantitative Evaluation of Fourier Components in Transparent and Opaque Calf Cornea, The American Journal of Anatomy (1991), 191:408–418.

(List continued on next page.)

*Primary Examiner*—Edward R. Cosimano
*Attorney, Agent, or Firm*—Christensen, O'Connor, Johnson & Kindness PLLC

[57] ABSTRACT

A system (10) is disclosed for use in detecting and analyzing cell and tissue microstructure as part of the diagnosis of a variety of pathological conditions, including cataracts, as well as aging, disease and certain traumatic events. The system includes a data input system (12), which may produce data regarding the microstructure to be evaluated either invasively or noninvasively. An electron microscope (20) may be employed to collect data regarding the microstructure of any tissue to be evaluated for the existence of a pathological condition. The system (12) also includes a computer (14) programmed to analyze the output of the data collection system by using signal processing techniques that are applicable to the data output characterizing the nonrandom microstructure. These techniques include fractal analysis, oscillatory analysis, and a modified Fourier/fractal analysis. The outcome of the signal processing is then compared to empirical data to effect a diagnosis.

47 Claims, 19 Drawing Sheets

OTHER PUBLICATIONS

Shahram Vaezy, Fourier Analysis of Electron Microscopy Images in the Study of Ocular Transparency, 1991, vol. 52/08B of Dissertation Abstracts International, p. 4337.

Xia Liu, Guowang and Martin D. Fox, Fractal Description and Classification of Breast Tumors, Annual International Conference of the IEEE Engineering in Medicine and Biology Society, 1991, vol. 13, No. 1, pp. 0112–0113.

P. Bock, C.J. Kocinski, H. Schmidt, R. Klinnert, R. Kober and R. Rovner, Sensitivity of ALIAS to Small Variations in the Dimension of Fractal Image, IJCNN International Joint Conference on Neural Networks, 1992, vol. 4, pp. 339–353.

G.B. Benedek, L.T. Chylack, Jr., T. Libondi, P. Magnante and M. Pennert, Quantitative Detection of the Molecular Changes Associated with Early Cataractogenesis in the Living Human Lens Using Quasielastic Light Scattering, Current Eye Research (1987), pp. 1421–1432.

*The Fractal Geometry of Nature*, Benoit B. Mandelbrot, pp. 247–255, W.H. Freeman and Company (1983).

*Chaos: Making a New Science*, James Gleick, Penguin Books (1987).

"Science in Pictures, Chaos and Fractals in Human Physiology," Ary L. Goldberger, David R. Rigney and Bruce J. West, *Scientific American,*, pp. 42–49 (Feb. 1990).

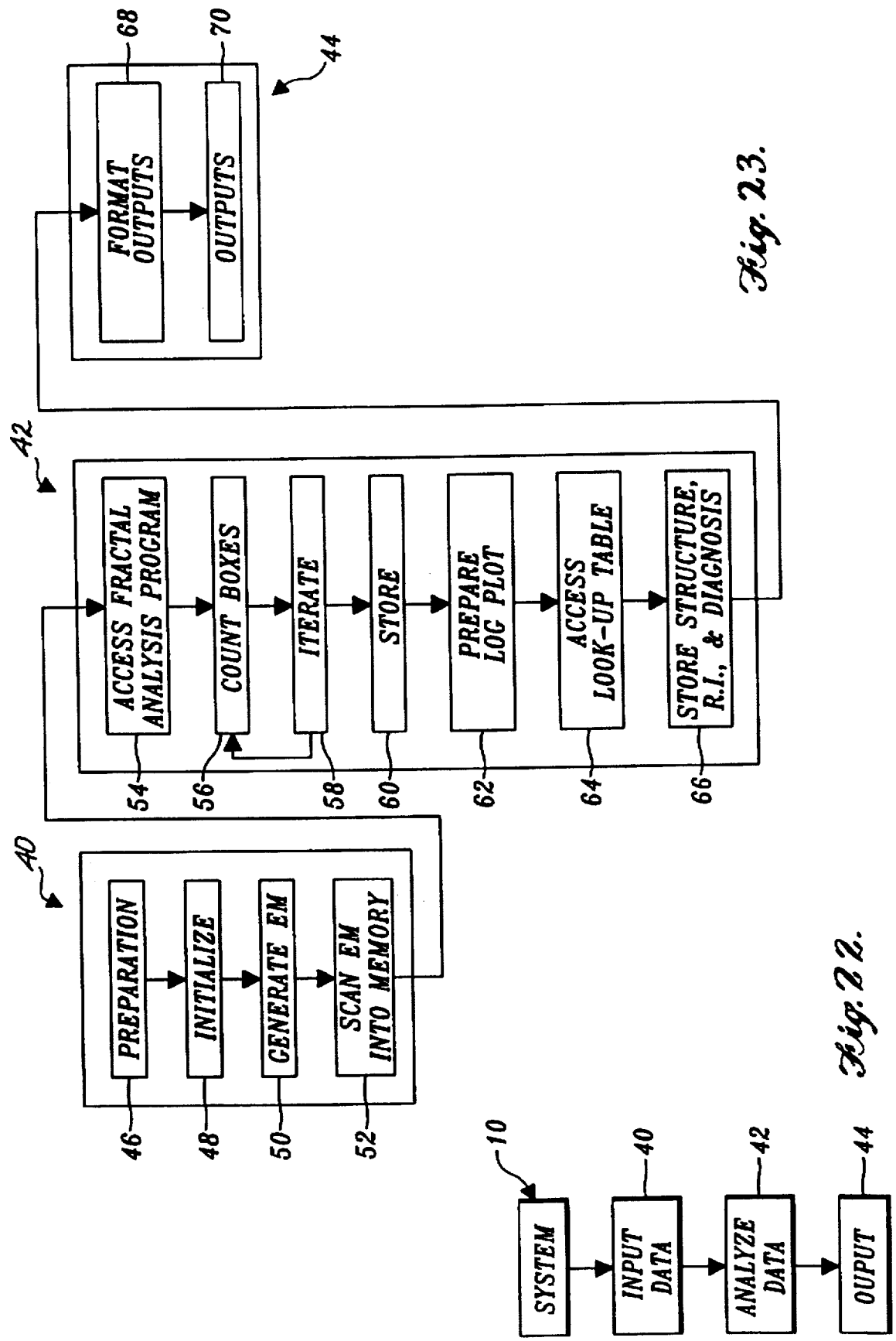

ORDER-BASED ANALYSES OF CELL AND TISSUE STRUCTURE

This is a national stage filling of PCT International Patent Application No. PCT/US92/12149 filed Dec. 14, 1993 and entitled ORDER-BASED ANALYSES OF CELL AND TISSUE STRUCTURE, which in turn, is a continuation-in-part of U.S. patent application Ser. No. 07/991,583, files Dec. 14, 1992, and entitled ORDER-BASED ANALYSES OF CELL AND TISSUE STRUCTURE, now abandoned. The subject matter of application Ser. No. 07/991,583 is incorporated herein by reference.

This invention was made with government support under Grant No. EY 04542 and EY 01730 awarded by the National Eye Institute. The government has certain rights in this invention.

FIELD OF THE INVENTION

This invention relates generally to the analysis of cell and tissue structure and, more particularly, to the use of such analyses in the diagnosis of conditions associated with variations in such structure.

BACKGROUND OF THE INVENTION

The evaluation of cell and tissue structure (hereinafter referred to as "microstructure") is of considerable importance to a variety of disciplines in the medical field. For example, the degeneration of microstructure may be associated with pathological conditions, traumatic events, and aging. While the effective treatment of these conditions often depends upon the early detection of the degenerative microstructure, conventional approaches to the identification of, for example, pathologically significant spatial fluctuations in cell density, have met with limited success.

One potentially useful application for the evaluation of microstructure is in the development of methods for diagnosis of cataracts. In a healthy eye, light from an object being viewed is sequentially focused upon the retina by the cornea and lens. The cornea is a fixed component responsible for the most of the refraction experienced by the light. The lens, on the other hand, is an adjustable component that is controlled by surrounding muscle fibers to ensure proper focusing of the image on the retina, regardless of the distance to the object being viewed.

Obviously, both the cornea and the lens must be transparent or vision will be impaired. While the microstructure of a healthy cornea or lens is organized for virtually complete transparency, this microstructure commonly degenerates, causing significant scattering of light and cornea or lens opacity. In lens tissue, this apparently irregular structural degeneration is known as cataracts and, in advanced stages, results in complete loss of sight.

FIGS. 1-5 illustrate the degeneration of the microstructure of a lens associated with cataracts. In that regard, FIG. 1 is an electron micrograph of a substantially transparent (i.e., cataract free) region of a lens, produced by an electron microscope at a magnification of 10k. As shown, the lens is composed of various cells C, having cell membranes M that enclose cytoplasm. Visual observation of FIGS. 1 and 2 indicates that the cell microstructure is organized in an apparently random fashion. The ability of the lens to transmit light without scattering, and, hence, the transparency of the lens, is dependent upon this structure.

FIGS. 3-5 are electron micrographs illustrating the spatial variations in microstructure and, hence, refractive index, associated with progressively more opaque regions of a lens. Visual observations suggests that the cell microstructure is organized in an apparently random fashion.

Given the limitations of visual evaluation, more advanced analytical techniques have been investigated. For example, signal processing techniques have been used to interpret the data collected by the electron microscope. In that regard, a digitized electron micrograph is an image formed from a 256-by-256 array of pixels, spatially representative of the region of the tissue section being imaged. Each pixel is assigned an intensity, or gray-scale value, ranging from zero to 255. This gray-scale value is representative of the density of the image associated with the corresponding tissue section and, hence, the cellular density at that section. The gray-scale data associated with one row of this array represents the variation in cellular density across one line scan of the biopsy. An illustrative line scan is plotted in FIG. 6.

Discussing now several types of signal processing techniques applied to the analysis of such line scans, Fourier transform methods have been used to detect the differences between line scans associated with normal, transparent microstructures and pathological, opaque microstructures. Details regarding the use of one-dimensional Fourier processing techniques are included in Vaezy et al, "A Quantitative Analysis of Transparency in the Human Sclera and Cornea Using Fourier Methods," 163 *Journal of Microscopy* 85–94 (1991) and Gisselberg et al., "A Quantitative Evaluation of Fourier Components in Transparent and Opaque Calf Cornea", 191 *American Journal of Anatomy* 408–418 (1991).

In that regard, the Fourier transform analysis of a line scan provides an energy spectrum showing the spatial frequency and amplitude of the Fourier components of the line scan. This process is repeated for each line scan and the results are combined and normalized to produce an energy spectrum for the entire video image, showing the relative contributions of the Fourier components to that image. An illustrative spectrum showing the magnitude of the Fourier components plotted as a function of frequency for a lens tissue is provided in FIG. 7.

As previously noted, cell and tissue transparency is inversely proportional to the amount of light scattered or absorbed by the associated microstructure. Light scattering is minimized when the principal Fourier components of the image have spatial dimensions (inverse of frequency) that are small relative to the wavelength of light to be transmitted. Thus, if the higher magnitude regions of the spectrum shown in FIG. 7 fall below a range of 200–1100 nanometers, the corresponding microstructure would be normal and transparent. The actual evaluation of the Fourier data may be performed by a statistical analysis of the spectrum based upon clinical data obtained from a known population of normal and diseased tissue.

In view of the apparently random nature of microstructure, efforts have also been made to apply correlation analysis to the interpretation of light scattering in human lens tissue. The techniques involved in this type of analysis are discussed in greater detail in, for example, Benedek et al., "Quantitative Detection of the Molecular Changes Associated with Early Cataractogenesis in the Living Human Lens Using Quasielastic Light Scattering", 6 *Current Eye Research* 1421–32 (1987).

Despite their promise in characterizing pathologically based spatial variations in microstructure, the signal processing techniques discussed above have limitations. In that regard, while the statistical analysis of spectral components identified by Fourier processing techniques provides an estimate of abnormal or pathological microstructure, the existence of a continuum of Fourier components in any microstructure, rather than a discrete number of components, makes it difficult to resolve or quantify the spectrum. It has been also suggested that patterns in spatial density fluctuations in transparent and opaque lens cytoplasm resemble fractal structures and that the transition between transparent and opaque cytoplasm may exhibit fractal growth See Vaezy, S., *Fourier Analysis of Election Microscopy Images in the Study of Ocular Transparency*, 166 (1991). Yet others have suggested that the concept of fractals be applied to images of breast tumors in order to describe the types of tumors pictured. See Liu et al., Fractal Description and Classification of Breast Tumors, 13 IEEE ENGINEERING IN MEDICINE AND BIOLOGY MAGAZINE, 112, 112–113 (1991). However, a technique has not been proposed or suggested that could use this information for accurately detecting and analyzing variations in microstructure for use in the diagnosis of pathological conditions.

In view of the preceding observations, it would be desirable to develop a method and apparatus for accurately detecting and analyzing spatial variations in microstructure for use in the development of methods for diagnosis and treatment of a variety of pathological conditions, including cataracts, as well as traumatic injuries and aging.

SUMMARY OF THE INVENTION

In accordance with this invention, various systems and methods are provided for evaluating the microstructure of cells and tissue. These systems and methods take advantage of the nonrandom nature of the microstructure of both normal and, for example, pathological tissue, allowing techniques previously deemed inapplicable to be employed.

In accordance with one embodiment of the invention, a system is provided for evaluating the microstructure of cells and tissue, and producing a diagnostic output indicative of the status of the microstructure. The system includes a data input system for producing a data output including information characterizing the nonrandom microstructure. A processing system is also included to convert the data output into a diagnostic output indicative of the microstructure using a technique based upon a representation of the nonrandom nature of the microstructure as a power law function. The power law function is expressed by the equation:

$$|A|^2 = (1/f)^\beta$$

where A is an amplitude of a Fourier component associated with the data output, f is a frequency of a Fourier component associated with the data output, and β is an exponent of the power law function In accordance with further aspects of the invention, the data input system may be any one of various different devices including an electron microscope, magnetic resonance imaging system, and NMR spectroscopy. Further, several different types of analyses may be performed on the data output. For example, a fractal analysis may be performed to produce a fractal dimension D as a quantified output indicative of the microstructure, where fractal dimension D is a function of the exponent β. Alternatively, an oscillatory analysis may be performed to produce a phase space plot associated with the data output, which is then convened into a quantified output indicative of the microstructure. As yet another alternative, a Fourier analysis of the data output can be performed and then analyzed to produce a fractal dimension for use as a quantified output of microstructure.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 22 is a flow chart depicting the three basic operations performed by the system of FIG. 21;

FIG. 23 is a more detailed flow chart illustrating the operations involved in the summary chart of FIG. 22;

FIGS. 51-56 are the log-log plots associated with the corresponding Fourier spectra of FIGS. 47-51;

DETAILED DESCRIPTION OF THE PREFERRED EMBODIMENT

Figure 20:
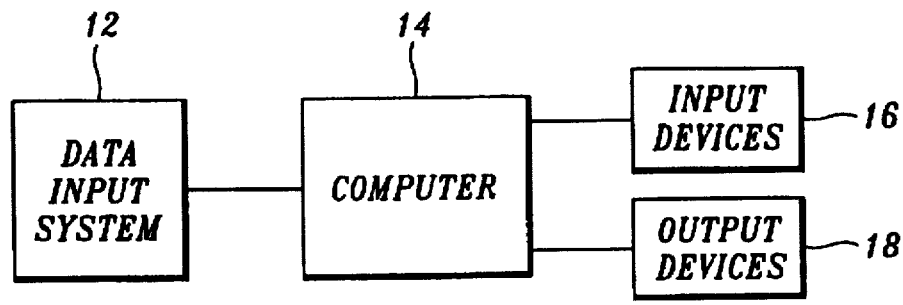
FIG. 20 is a block diagram of a system constructed in accordance with this invention for use in detecting and analyzing spatial variations in microstructure to diagnose, for example, pathological conditions, traumatic events, and aging.

Referring now to FIG. 20, a diagnostic system 10, constructed in accordance with this invention, is shown for use in detecting and analyzing spatial variations in microstructure. This analysis is further used to develop a method to diagnose, for example, pathological conditions associated with altered microstructure, or the effect of aging and perhaps even traumatic events. As will be described in greater detail below, an important aspect of system 10 is its ability to take advantage of certain signal processing techniques based upon the nonrandom nature of both normal and degenerated microstructure of any type.

Figure 1:
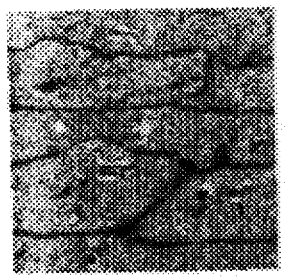
FIGS. 1–5 are a series of electron micrographs taken from a cataractus lens tissue growing progressively more opaque from its periphery to its center.
Figure 2:
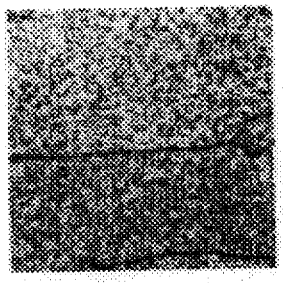
Figure 3:
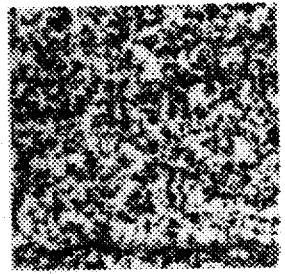
Figure 4:
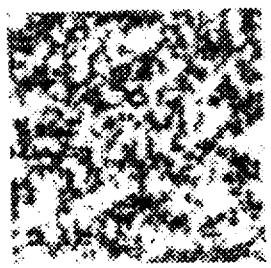
Figure 5:
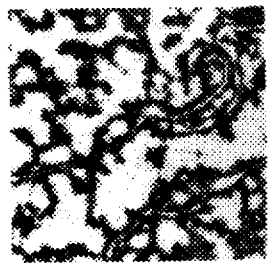
Figure 6:
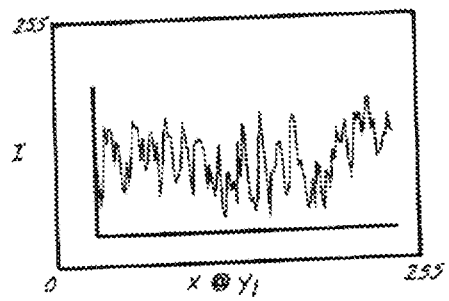
FIG. 6 is a line scan associated with the electron micrograph of FIG. 1, providing/a plot of image intensity for a select row of the micrograph, which is representative of cellular density along the corresponding portion of the lens.
Figure 7:
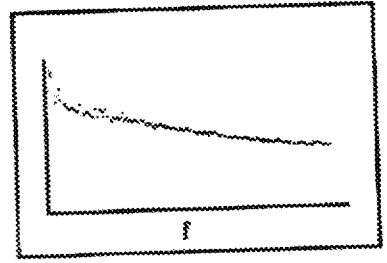
FIG. 7 is a graph illustrating the contributions of the various Fourier or spectral components to the image provided in an electron micrograph of a lens.

Conventional wisdom held that microstructure was randomly organized both in most normal and pathological tissue. The apparent correctness of this position can be confirmed by simple observation of microstructure via an electron microscope. As shown in the electron micrographs of FIGS. 1-5, lens microstructure exhibits no clear order at any stage of cataracts and, instead, appears entirely random. Observation of the line scan of FIG. 6 further suggests the random nature of the microstructure.

As noted above, system 10 takes advantage of applicants' discovery that microstructure is in fact neither random nor highly ordered for normal and pathological tissues of all types, rather, micro structure is nonrandom and fractal in nature. Microstructure exhibits properties of a concept known in fractal geometry as "self-similarity." A shape is self-similar when each piece of its shape is geometrically similar to the whole. For example, one can isolate and examine a smaller, scaled portion of a microstructure. The details of the microstructure at this smaller scale are similar to the details of same the microstructure examined on a larger or an even smaller scale. The applicants have discovered that all microstructures have this internal, look-alike property called self-similarity. Consequently, the nature of the microstructure is nonrandom and fractal. The nonrandom and fractal nature of the microstructure has also been confirmed by the self-similarity of line scans associated with electron micrographs of the microstructure. In that regard, if a segment of the line scan is excerpted and plotted on an expanded spatial scale, the expanded excerpt will be similar to the original line scan if it is a nonrandom fractal. Consequently, fractal analysis may be used to interpret the line scan. For further discussion regarding the self, similarity property of fractals see Goldberger, et al., "Chaos and Fractals in Human Physiology," *Scientific American*, 42 (Feb. 1990).

In addition to recognizing that the nature of the microstructure is nonrandom, applicant has discovered that the nonrandom nature of micro structure can be characterized as 1/f noise using the low power law function:

$$|A|^2 = (1/f)^\beta \qquad (1)$$

where A is the amplitude of a Fourier component of a line scan associated with the microstructure, f is the frequency of the Fourier component of a line scan, $\beta$ is the exponent of the reciprocal of the frequency, and 1/f noise is fractal in nature.

Figure 8:
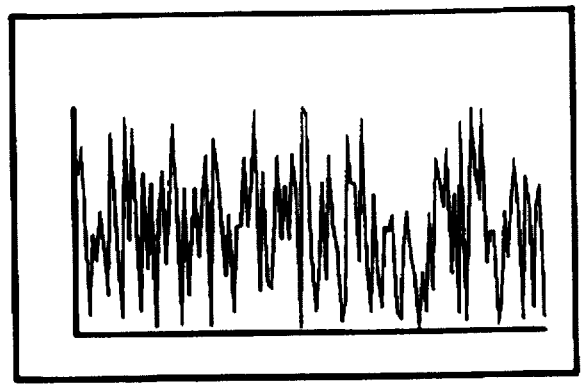
FIG. 8 is a graph depicting completely random white noise.
Figure 9:
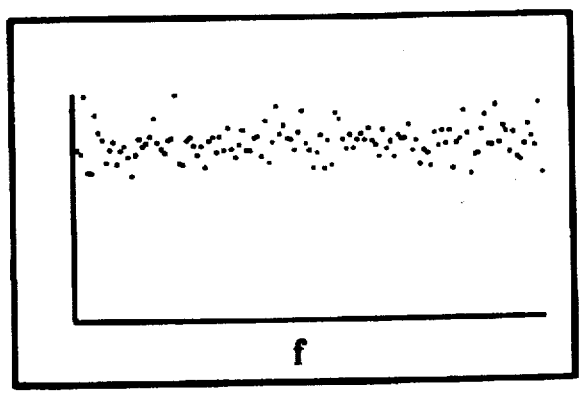
FIG. 9 is a graph illustrating the Fourier energy spectrum associated with white noise.
Figure 10:
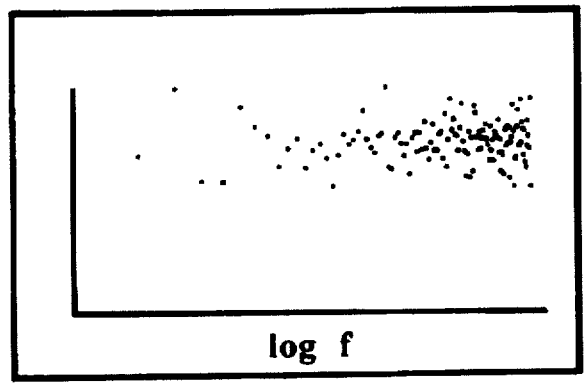
FIG. 10 is a log-log plot depicting the spectral density associated with white noise.
Figure 16:
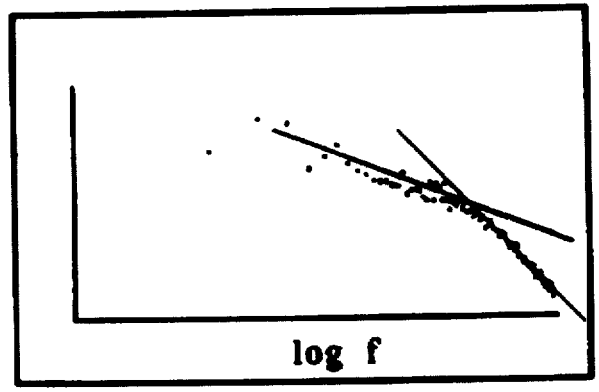
FIG. 16 is a a log-log plot depicting the spectral density associated with line scan.
Figure 17:
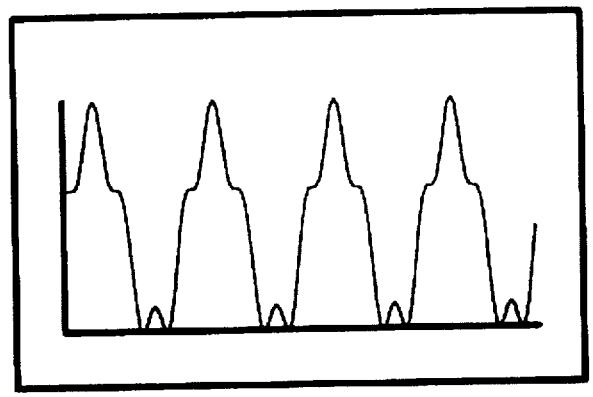
FIG. 17 is a graph depicting highly ordered structure.
Figure 18:
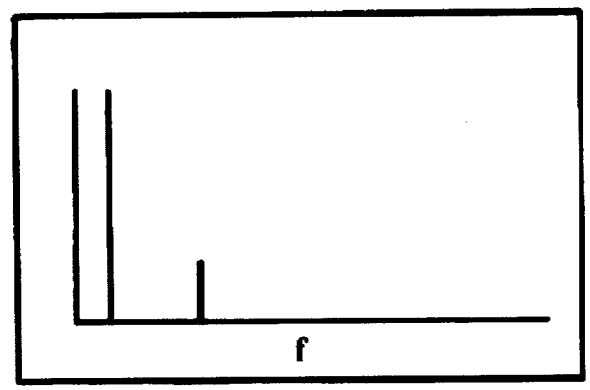
FIG. 18 is a graph illustrating the Fourier energy spectrum associated with a highly ordered structure.
Figure 19:
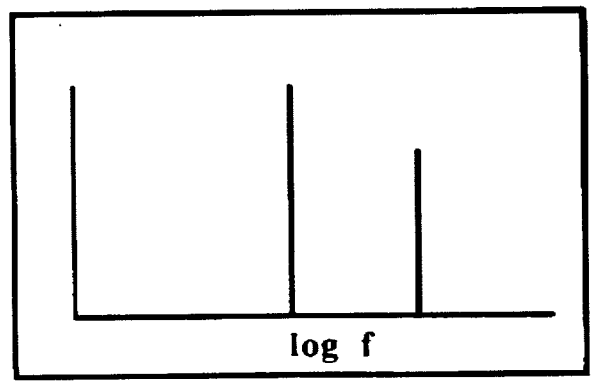
FIG. 19 is a log-log plot depicting the spectral density associated with highly ordered noise.

As seen in FIGS. 8-19, 1/f noise represents an intermediate type of structure that falls somewhere between completely random noise, known as "white noise," and highly ordered structure. White noise, as shown in FIG. 8, can be produced by a random number generator and is completely uncorrelated from point to point. Its spectral density is depicted by both the Fourier spectrum and the log-log plot of the Fourier spectrum shown in FIGS. 9 and 10, respectively. The spectral density for white noise is exhibited by a relatively uniform distribution of coordinate pairs along a flat horizontal line. This represents equal contributions of all frequencies, like the frequencies of white light. In contrast, FIG. 17 shows the graph associated With highly ordered structure. Highly ordered structure exhibits completely ordered fluctuation with exact and repeating points. The spectral density of highly ordered structure is depicted by a pair of vertical lines as shown in FIGS. 18 and 19.

Figure 11:
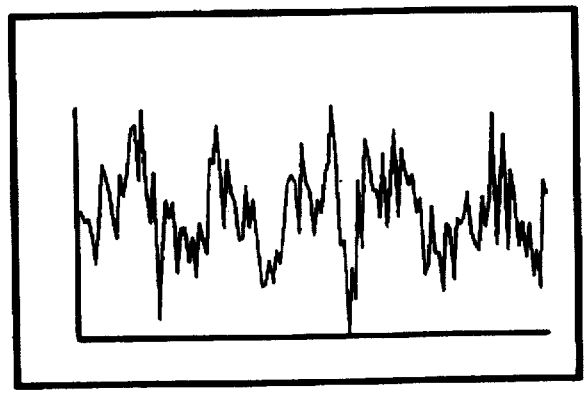
FIG. 11 is a graph depicting 1/f noise.
Figure 12:
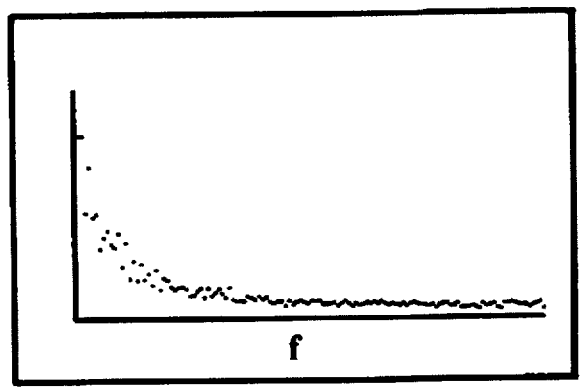
FIG. 12 is a graph illustrating the Fourier energy spectrum associated with 1/f noise.
Figure 13:
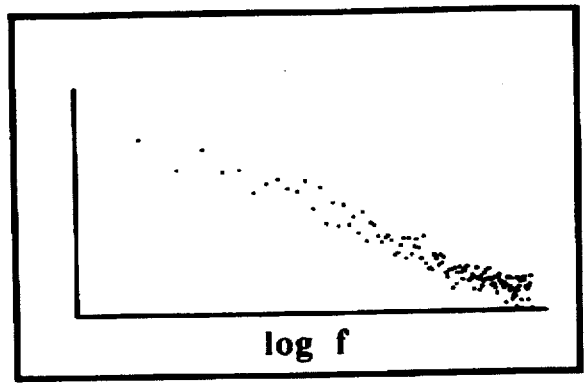
FIG. 13 a log-log plot depicting the spectral density associated with 1/f noise.

As shown in FIG. 11, 1/f noise falls in between these types of structures. The waveform depicting of 1/f noise exhibits complex fluctuation, more resembling natural fluctuation than random fluctuation. Waveforms that depict such fluctuation can be defined as fractal signals. The spectral density of the waveform shown in FIG. 11 is depicted by the Fourier spectrum and the log-log plot shown in FIGS. 12 and 13, respectively. As seen in FIG. 13, the log-log plot depicting spectral density of 1/f noise exhibits a relatively uniform distribution of coordinate pairs along a sloping line. In general, the term 1/f noise applies to any fluctuating noise with spectral density exhibiting such a relatively uniform distribution of coordinate pairs along a sloping line. The slope of the line is characterized by a number which is the negative of $\beta$. Therefore, the spectral density and the slope of the line about which the coordinate pairs are distributed will vary as the exponent $\beta$ of the power law function varies for different types of 1/f noise.

There are no simple mathematical models that produce 1/f noise. Little is known about the physical origins of 1/f noise, but it is found in many physical systems: in almost all electronic components from simple carbon resistors to vacuum tubes and all semiconducting devices; in all time standards; in ocean flows; and in music. Additional details regarding 1/f noise can be found in Voss, K. F., *Fractals in Nature: From Characterization to Simulation*, in Science of Fractal Images 39 (1988). Applicants, however, have discovered that 1/f noise is also present in cell and tissue microstructure.

Figure 14:
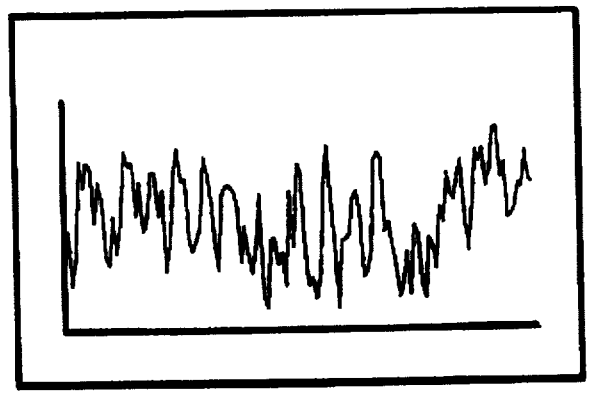
FIG. 14 is a line scan associated with the electron micrograph of FIG. 1, providing a plot of image density for a select row of micrograph, which is representative of cellular density along the corresponding portion of the lens.
Figure 15:
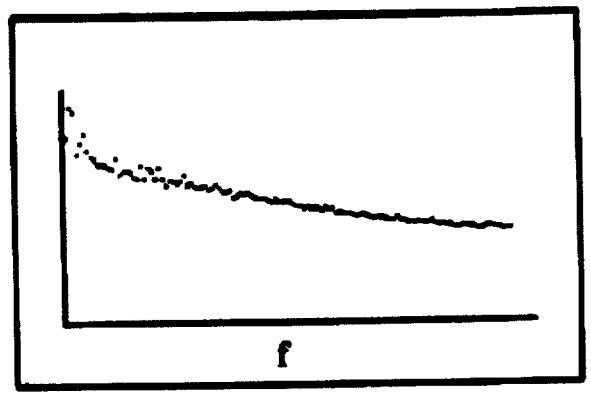
FIG. 15 is a graph illustrating the Fourier energy spectrum associated with the line scan.

A line scan of an electron micrograph image of lens tissue is shown in FIG. 14. The line scan closely resembles the waveform of 1/f noise, and exhibits a natural fluctuation which has some degree of order. Therefore, the line scan can be defined as a fractal signal. As shown in FIGS. 15 and 16, the spectral density associated with the microstructure is also similar to that associated with 1/f noise. In other words, the log-log plot associated with the microstructure exhibits a general distribution of coordinate pairs along a sloping line, just like the log-log plot associated with 1/f noise. However, lens tissue is more complex. Therefore, the line produced in the log-log plot associated with the microstructure has two components, with each component having its own slope, β. Consequently, each slope of the log-log plot and the spectral density associated with the microstructure will vary as some function of each exponent β. The key, here, is to recognize that this means that exponent β varies as the density and, hence, status of the microstructure varies.

In addition, the same relationship exists for any type of cell and tissue microstructure. However, microstructure exists that is even more complex than lens microstructure. In such cases, the log-log plot associated with the microstructure will exhibit a general distribution of coordinate pairs along a sloping line having multiple components. Thus, the slope of each component of the line will vary as a some function of each corresponding exponent β.

As noted above, the line scan can be characterized as a fractal signal because microstructure can be characterized as 1/f noise. Fractal signals generally have a broad energy spectrum that can be described by the power law function of equation (1). Thus, the nonrandom nature of microstructure can be characterized as 1/f noise using the power law function of equation (1). Further, the status of that microstructure can be characterized by determining a value for the function of exponent β that indicates the status of the microstructure.

Having briefly reviewed one of the important bases for the operation of system 10, its construction and operation will now be reviewed in greater detail. As will be appreciated, the system 10 can be constructed for use in diagnosing any of a variety of pathological conditions, such as cancer, inherited disorders of connective tissue and organs including the liver, as well as aging and trauma. For the purposes of the ensuing discussion, however, the system 10 will be described for use in the development of methods for diagnosing cataracts.

As shown in FIG. 20, the system 10 includes a data input system 12, computer 14, input devices 16, and output devices 18. The data input system 12 is designed to provide data representative of the microstructure of ocular tissue to be evaluated. The output of the data input system 12 is, in turn, applied to the computer 14, which is programmed to analyze the output to (a) evaluate the microstructure of the ocular tissue and (b) develop methods for diagnosing the existence and extent of abnormal lens structure. The computer provides various outputs representative of the analysis and diagnosis to, for example, attending medical personnel via output devices 18. Inputs are similarly provided to computer 14 via input devices 16.

Figure 21:
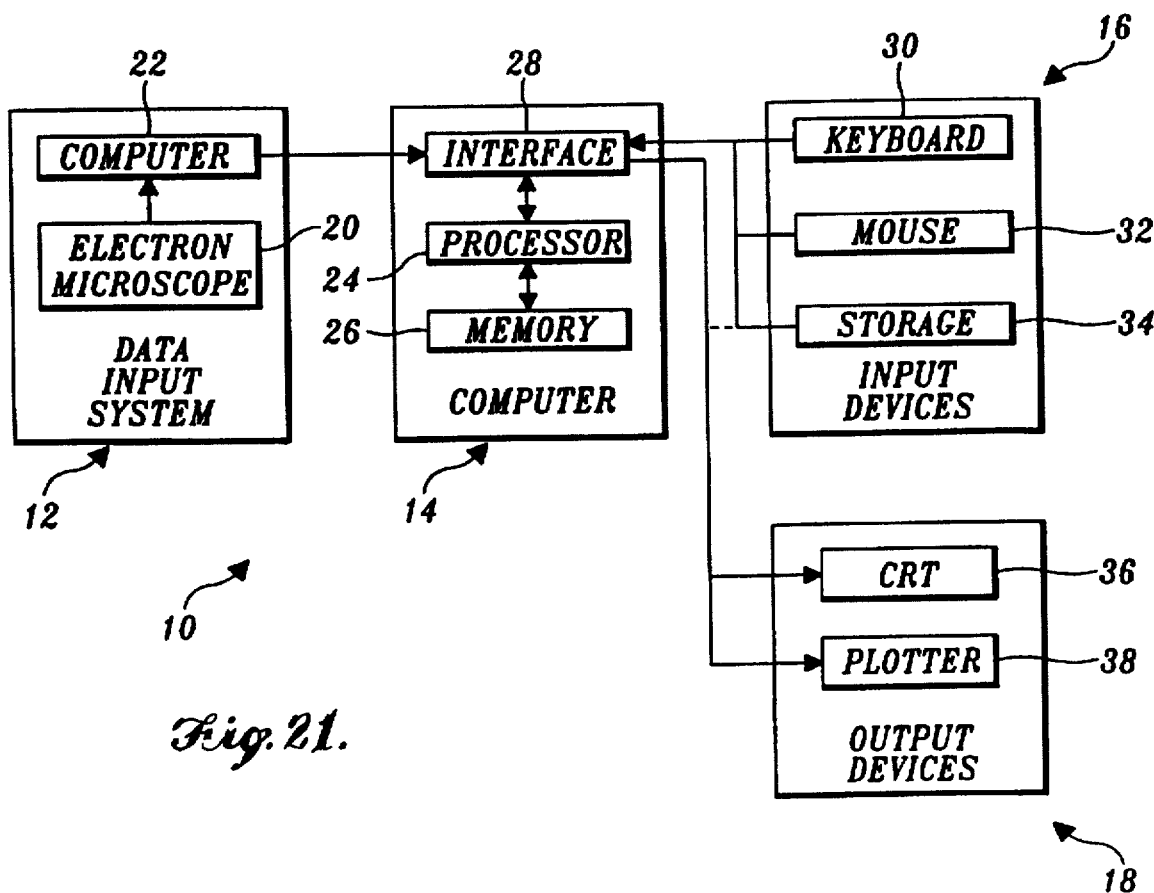
FIG. 21 is a more detailed block diagram of one embodiment of the system shown in FIG. 20.

Reviewing the construction of each of these components individually, in one embodiment of system 10 shown in FIG. 21, the data input system 12 includes an electron microscope 20, that is controlled by an independent computer 22. The electron microscope 20 is, for example, of the type sold by JEOL Ltd., Tokyo, Japan, under the trademark JEM 1200EX.

The microscope 20 is operated by computer 22 in a "scanning transmission electron microscopy" mode to gather video images of a sample of any tissue presented for examination on the microscope's stage. More particularly, microscope 20 collects an electron micrograph image, which is then digitized into a 256-by-256 pixel image, with each pixel assigned an intensity or gray-scale value of 0 to 255. A representative magnification of 10k may be used, falling within a range of, for example, 5k to 40k that is useful in the evaluation of cataracts. The resultant image, which is effectively a density map of the microstructure of the sample, is stored in the memory of computer 22 and displayed on a cathode ray tube (CRT) display provided on microscope 20.

Various alternative data input systems 12 can be put in place of the electron microscope 20 and computer 22 described above. For example, a magnetic resonance imaging (MKI) system may be used to generate cross sectional images of tissue, corresponding to the electron micrographs described above. With suitable processing incorporated into the system, the output of the MRI system can directly be substituted as the input to computer 14. Another alternative is to use a nuclear magnetic resonance (NMR) spectrometer to noninvasively collect data regarding the intensity of light scattered by the ocular tissue of interest.

Each of the embodiments of input system 12 described above is designed to examine a tissue sample of any type and provide data to computer 14 based upon that examination. However, the system 12 may also be employed to input previously or externally collected data. For example, the input system 12 may include an image digitizer constructed to scan previously collected electron micrographs, or photographs of microstructure, and digitize them for input to computer 14.

Turning now to the computer 14, it is, for example, an IBM/AT compatible computer including, in part, a 80386 processor 24, five megabyte memory 26, and suitable interface 28. The processor 24 is responsible for analyzing the input data and providing the desired outputs in response to a variety of program instructions. Memory 26 is responsible for storing the software instructions, along with data inputs to, and outputs from, processor 24. The interface 28 provides the desired communication link between processor 24 and the remainder of the system 10.

As shown in FIG. 21, the input devices 16 include, for example, a keyboard 30 and mouse 32 that allow the user to provide various inputs to system 10, including, for example, data associated with the biopsies evaluated and other information required to initialize the analyses performed by processor 24. A mass storage device 34, or auxiliary computer, may also be employed as an input device to download alternative files of clinically obtained empirical data for use by processor 24, as described in greater detail below.

The output devices 18 include, for example, a cathode ray tube (CRT) 36 and plotter 38, both of which can be used to display the electron micrographs produced by microscope 20. These displays may be annotated with additional information regarding the analysis performed by processor 24, or alternative displays may be produced to convey that information, as will be described in greater detail below. Also, as indicated by the dotted line in FIG. 21, the storage device or auxiliary computer 34 included in the input devices may also be used to store outputs from processor 24.

Having reviewed the basic construction of system 10, its operation will now be considered. In that regard, as indicated by the simplified operational flow chart of FIG. 22, the system 10 initially inputs digitized data during a data input routine 40. Then, during a processing routine 42, the data is analyzed to evaluate the microstructure of the tissue sample and to develop methods for diagnosis of pathological conditions. Finally, an output routine 44 causes the system 10 to provide the operator with the results of the analysis and diagnosis.

As shown in FIG. 23, prior to the initiation of the data input routine 40 by processor 24, a suitable sample of tissue is obtained and arranged on the electron microscope stage for analysis at a block 46. Then, at block 48, the operation of processor 24 in response to the software stored in memory 26 is initialized. At block 50, processor 24 instructs the computer 22 controlling electron microscope 20 to collect the data required to generate an electron micrograph (EM). The video image associated with the EM is then digitized and scanned into the memory 26 of computer 14 at block 52.

As will be appreciated, the data input routine 40 may be altered in various ways. For example, if a noninvasive data input system 12 is employed, the step of obtaining the tissue sample can be eliminated and the entire data input process may be immediately repeated for additional samples of the same or adjacent tissue. Also, the data input routine 40 may be performed independent of routines 42 and 44, with the data collected simply being stored for analysis at some other time. As yet another alternative, the data input routine 40 may simply be employed to convert previously collected data, such as a photograph, into a format suitable for processing by computer 14.

Turning now to the data analysis routine 42, the first of several alternative embodiments is also shown in greater detail in FIG. 23. Routine 42 includes, at block 54, the preliminary step of accessing a fractal analysis program stored in memory 26.

As discussed above, the nonrandom nature of the microstructure can be characterized as 1/f noise. Therefore, the line scan associated with the microstructure is a fractal signal. The fractal analysis performed by the software package is used to compute a fractal dimension D. Fractal dimension D characterizes the fractal signal represented by the line scan or the image as a whole. Fractal dimension D is the dimension indicating the self-similarity of the microstructure being analyzed. Therefore, fractal dimension D changes as the organization of the microstructure changes. There is a direct relationship between the fractal dimension D and the logarithmic slope of the spectral density of 1/f noise. The logarithmic slope of spectral density of 1/f noise varies with exponent β of the power law function of equation (1), therefore fractal dimension D will also vary as a function of the exponent β.

In a one-dimensional analysis of the line scan, the fractal dimension D is determined using a box counting technique, in which each iteration decreases the size of the "boxes" used to characterize the line scan. More particularly, the process begins by normalizing the line scan to have a maximum amplitude variation ranging from 0–1, rather than the 0–255 range associated with the gray scale. Normalization is performed because the characteristic of interest is the relative change in line scan amplitude, not the absolute value of that amplitude. However, if the variation in amplitude contributes to the fractal dimension, this normalization would not be performed.

Figure 24:
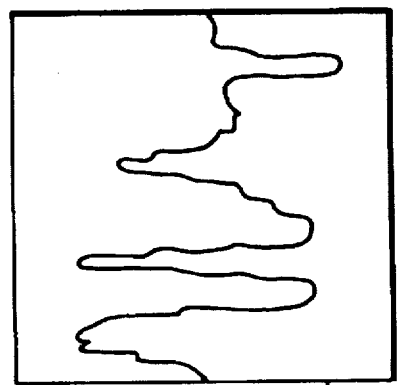

Box counting begins by considering the normal line scan as being enclosed by a first square box $b_1$, covering the entire grid the line scan is plotted on, as shown in FIG. 24. The size $\epsilon_1$ of box $b_1$ is equal to the length $x_1$ of the line scan included within box $b_1$. Because a single box is employed, the number n of boxes through which the line scan passes is equal to one.

Figure 25:
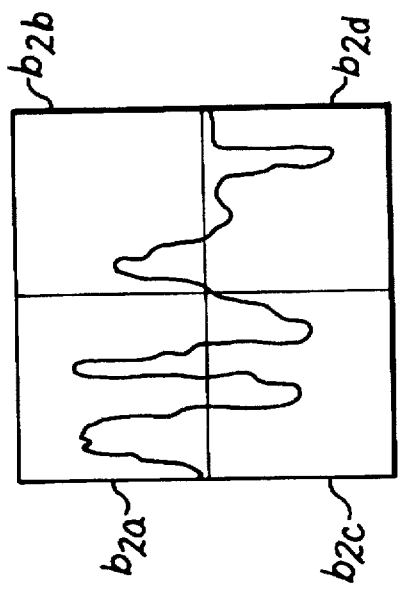
FIGS. 24, 25 and 26 illustrate the operation of a box counting step performed in the an of FIG. 23.

Next, box $b_1$ is divided into an equal number (i.e., four) of smaller square boxes $b_{2a}$, $b_{2b}$, $b_{2c}$, and $b_{2d}$, as shown in FIG. 25. Thus, the size $\epsilon_2$ of each box is now one-half the original length of the line scan. As shown, the line scan passes through all four boxes $b_{2a}$, $b_{2b}$, $b_{2c}$, and $b_{2d}$. Thus, the number n of boxes counted is equal to four.

Figure 26:
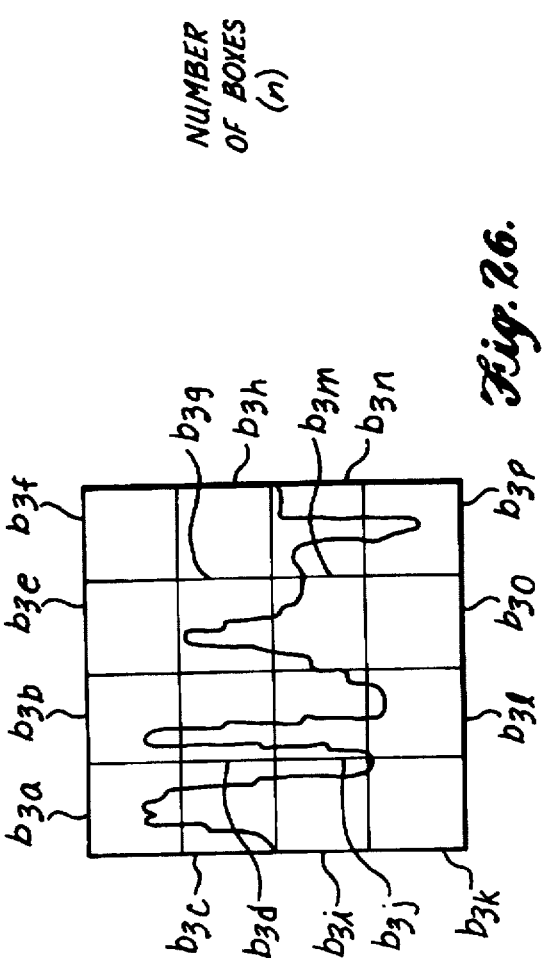

Again, each of the boxes the line scan passes through is divided into an equal number (i.e., four) of square boxes. Thus, box $b_{2a}$ is divided into boxes $b_{3a}$, $b_{3b}$, $b_{3c}$, and $b_{3d}$. Similarly, box $b_{2b}$ is divided into boxes $b_{3e}$, $b_{3f}$, $b_{3g}$, and $b_{3h}$; box $b_{2c}$ is divided into boxes $b_{3i}$, $b_{3j}$, $b_{3k}$, and $b_{3l}$; and box $b_{2d}$ is divided into boxes $b_{3m}$, $b_{3n}$, $b_{3o}$ and $b_{3p}$, as shown in FIG. 26. The size $\epsilon_3$ of each box is now one-fourth the original length of the line scan. As shown, the line scan passes through eleven of the boxes. Thus, the number n of boxes counted is equal to 11.

This process is repeated until the box size is equal to one pixel, i.e., the box size is 1/256 the original length of the line scan. The fractal dimension D can then be determined in accordance with the expression $$D = \lim_{\epsilon \to zero} \frac{\log n}{\log(1/\epsilon)} \quad (2)$$

where ε is the "size" of a box and n is the number of boxes through which the line scan passes. Although the fractal dimension D will be the same for two line scans or images associated with identical fractal cell structures, it provides a sensitive indicia of minor differences in microstructure not readily apparent in the line scans or images themselves.

Expressed in alternative fashion, the fractal analysis performed by the software package exploits the statistical self-similarity of the fractal line scans or images. Even though the details regarding microstructure conveyed by a line scan may be difficult to assess, the self-similarity and status of the structure can be readily quantified in fractal dimension D to allow easier and more accurate observations of microstructure. Additional details regarding fractal analysis can be found in, for example, Mandelbrot, *The Fractal Geometry of Nature*, W. H. Freeman & Co. (1983).

Returning to the operation of processor 24, in the preferred arrangement, the fractal analysis software initiates its operation at block 56. The analysis may be performed in a single dimension associated with a line scan, in two dimensions associated with the entire image, or in three dimensions associated with a three-dimensional cross-section of cells.

As for the two-dimensional analysis, at block 56, "box counting" is performed and iteratively repeated at block 58 to determine values of n and g for each iteration. However, the image actually analyzed represents a three-dimensional surface having peaks and valleys. Peaks represent areas of high cellular density and valleys represent areas of low cellular density. The "boxes" in this case are actually cubes of dimension ε that must cover the surface represented by the image. The number n and dimension ε of the cubes for each iteration are then stored in memory 26 at block 60.

Figure 27:
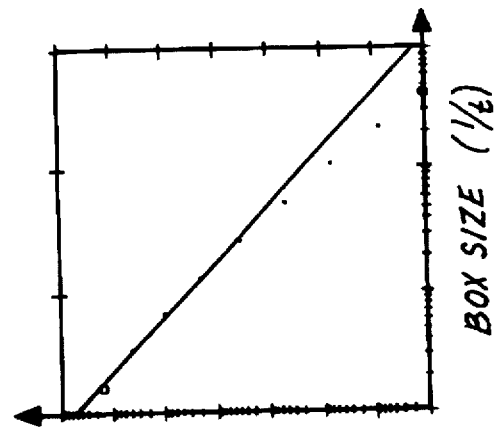
FIG. 27 is a log-log plot used to compute a fractal dimension D in accordance with a fractal analysis technique implemented by the system of FIG. 21.

Next, a plot of the log of the number n of cubes versus the log of the inverse of cube dimension ε is prepared at block 62. A representative log-log plot is shown in FIG. 27. As will be appreciated from equation (2), the slope of the resultant plot provides an estimate of the fractal dimension D and is stored in memory 26. As noted above this fractal dimension D provides a sensitive indication of the organization of the microstructure in the ocular tissue being examined.

As for the three-dimensional fractal analysis, it is conducted on several images representing a three-dimensional cross-section of cells. Consequently, the images represent the three-dimensional spatial density fluctuations across the entire cross-section of cells.

To evaluate the microstructure and develop a method for diagnosing of cataracts, the processor 24 is next instructed to compare the fractal dimension D obtained via the foregoing analysis with fractal dimensions empirically collected from a known population of normal and pathological tissue samples. In the single diseased lens shown in FIGS. 1-5, the extent of the opacity is proportional to distance from the lens' edge, and a range of empirical data can be obtained from a single such lens. Based upon such analyses, the fractal dimension D for normal transparent tissue has preliminarily been found to range between 1.6 and 1.8, while the fractal dimension for pathological opaque tissue ranges between 1.2 and 1.4. Also, as a preliminary result a 20 percent change in the fractal dimension of a transparent cell has been found to result in a change in the microstructure which indicates opacity.

The actual comparison of the fractal dimension D against the empirical data is performed at block 64 by consulting a look-up table associating narrow ranges of fractal dimensions with (a) microstructure, (b) light scattering associated with the cellular structures, and (c) a diagnosis of cataracts based upon (a) and (b). The specific microstructure, scattering, and diagnosis associated with the fractal dimension D are then stored at block 66, with the previously stored log plot and value for D, completing the data analysis routine 42.

With the analysis finished, the processor 24 is then directed to the output routine 44. There, at block 68, the various stored parameters computed above are formatted so that they are suitable for use by the output devices 18. Then, at block 70, outputs including the log plot, fractal dimension, indicia of microstructure, light scattering, and diagnosis are applied to output devices 18.

Figure 28:
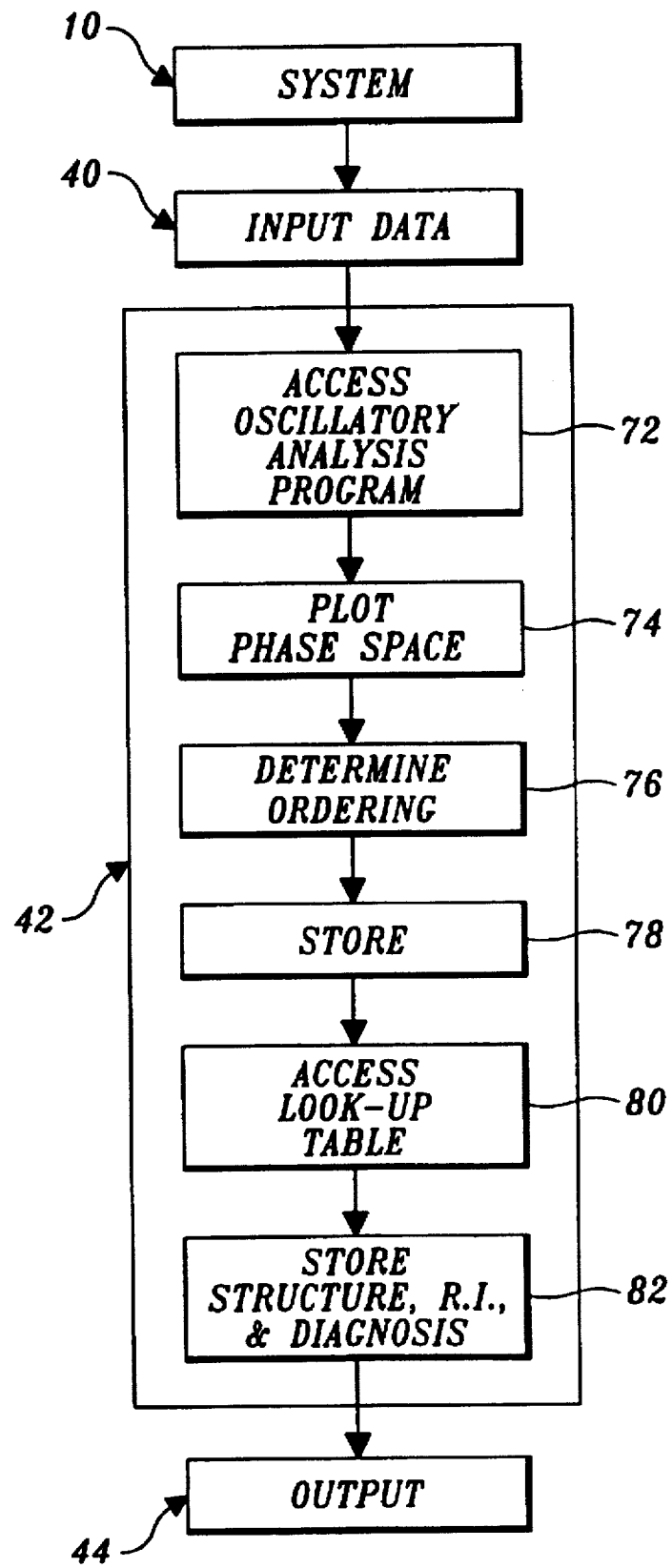
FIG. 28 is a flow chart illustrating an oscillatory analysis alternative to the analysis routine depicted in the flow chart of FIG. 23.
Figure 29:
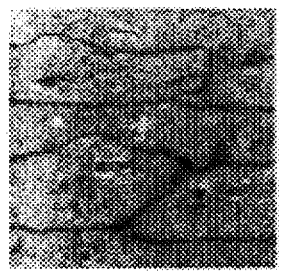
FIGS. 29–33 are a series from electron micrographs taken of a cataractus lens tissue growing more opaque from its periphery to its center.
Figure 30:
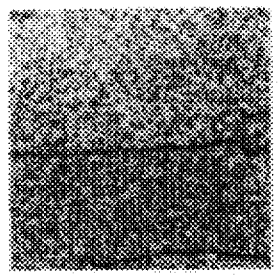
Figure 31:
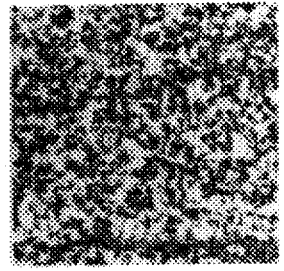

As previously noted, an alternative exists to the fractal processing routine 42 discussed above. In that regard, as shown in FIG. 28, a spatially dynamical or chaos (referred to herein as "oscillatory") analysis routine may be employed to link the data collection and output routines 40 and 44. Oscillatory analysis is another tool for analyzing systems including fractal systems. Therefore, this analysis can also be used to evaluate cell and tissue microstructure of any type. This oscillatory routine, includes, as a first step shown at block 72, the accessing of an oscillatory analysis program stored in memory 26.

The basic objective of the analysis to be performed by this software is to exploit the spatially dynamical or oscillatory nature of the line scans and image by assessing the correlation of spatially related data. The correlated relationship is then used to produce a phase space map representative of a degree of order in the system at block 74. An alternate explanation is that the phase space map describes the structural organization of nonrandom or random structures. As suggested above, the degree of order in the fractal system and associated with the phase space map is related to the exponent β of the power law function in equation (1). A more detailed discussion of dynamical theory is found in, for example, Gleick, *Chaos, Making a New Science* (1987).

Figure 34:
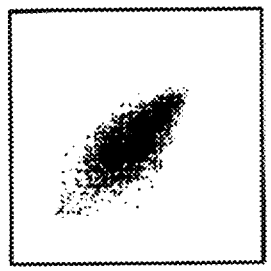
FIGS. 34-38 are a series of phase space plots used to assess the degree of order of the corresponding microstructures of FIGS. 29-33 with an oscillatory analyses technique implemented by the system of FIG. 21.
Figure 35:
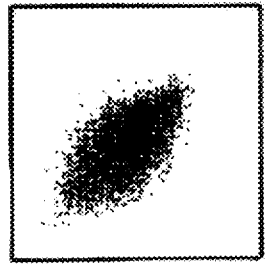
Figure 36:
Figure 32:
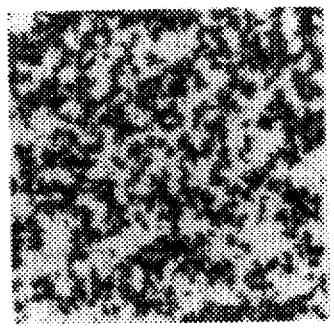
Figure 33:
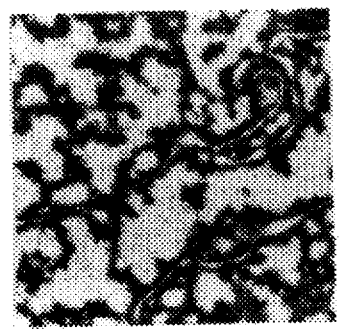
Figure 37:
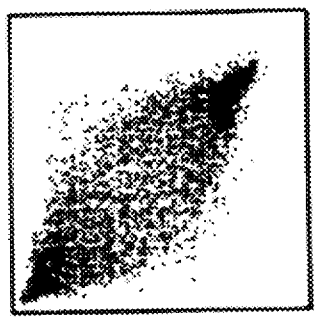

Returning to the operation of the processor 24 in accordance with the dynamical analysis program, at block 74, the processor 24 analyzes a first line scan to produce a phase space plot of the type shown in FIG. 34. The line scan is plot of intensity I as a function of some position x. At block 74, the processor 24 constructs the phase space plot by charting the coordinate pairs (I(x), I(x+τ)) for all integer values of x and one select integer value for τ. Thus, for example, if τ=1, the first point on the phase space plot corresponding to x=1 has an abscissa equal to the intensity I(1) of the line scan at the first pixel and an ordinate equal to the intensity I(2) of the line scan at the adjacent pixel. The next point is then plotted at (I(2), I(3)), with subsequent points plotted in similar fashion. As will be appreciated, if τ=2, the intensities used in plotting a given coordinate pair would be associated with pixels separated by one pixel.

Figure 38:
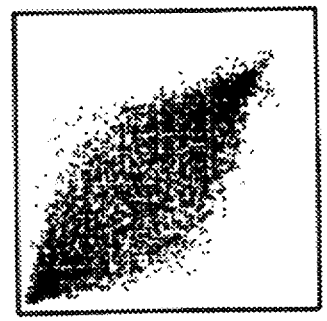
Figure 39:
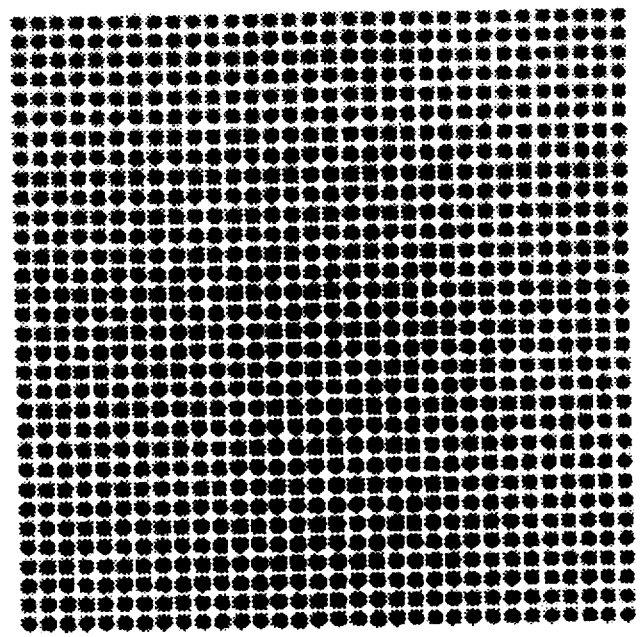
FIG. 39 is a picture of a highly ordered microstructure.
Figure 40:
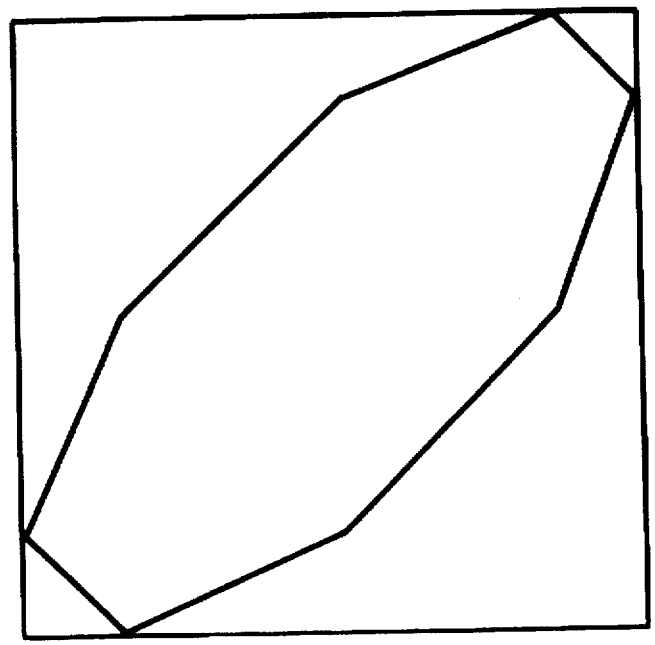
FIG. 40 is a phase space plot associated with a line scan of FIG. 39.

As pictured in FIG. 39, a highly ordered structure has a highly ordered graph. Consequently, when the microstructure is highly ordered, all of the points plotted on the phase space plot will fall along a well-defined curve as shown in FIG. 40. In contrast, if a line scan is a randomly varying signal representative of a microstructure that is entirely disordered, the phase space plot will exhibit a relatively uniform distribution of coordinate pairs. The phase plot of nonrandom microstructure will fall somewhere between these two extremes and is indicative of the nonrandom and fractal nature of the structure. Phase space plots associated with the electron micrographs of a cataractus lens shown in FIGS. 28-33 exhibit this behavior and are shown in FIGS. 34-38, respectively.

Once the phase space plot has been prepared at block 74, it is evaluated to determine the degree of order in the structure at block 76. In that regard, FIGS. 35-38 illustrate the relative difference between the phase space plots of a transparent tissue growing more opaque from its periphery to its center. As shown, a more pronounced compaction of data points around one region exists in the phase space plot of FIG. 35, which is consistent with the existence of transparent tissue. If there is a pronounced compaction of data points in two regions of the phase space plot, as shown in FIG. 38, then the existence of opaque lens tissue is indicated. Consequently, the distribution of coordinate pairs in the phase space plots can be used to assess the status of microstructure.

Several alternative techniques can be used to determine the orderliness of the microstructure at block 76. In that regard, the construction of phase space plots performed at block 74 may be repeated for increasingly larger values of τ. The phase space plots are then evaluated to determine the value of τ that first indicates a lack of correlation between the pixels involved due to their physical separation. In other words, phase space plots are produced for increasingly greater values of τ to determine the lowest value of τ for which the phase space plot does not appreciably change, when compared to the phase space plot for the preceding value of τ. By way of illustration, it may turn out that the phase space plot changes appreciably as τ is increased from nine to ten, but not as τ increases from ten to eleven. As a result, a value of τ equal to ten would be used to characterize the microstructure.

As will be appreciated, the value of τ used to characterize the microstructure varies with the degeneration and loss of order in the microstructure associated with, for example, cataracts. For a magnification of 10k, a characteristic value of τ less than or equal to ten is indicative of a transparent microstructure, while a value greater than or equal to fifteen is indicative of a microstructure that will introduce significant light scatterings.

As an alternative to the use of a value of x to characterize the microstructure, the phase space plots may be analyzed by their general shape. In that regard, the "length" and "width" of a phase space plot may be computed and used, along with the angular orientation of the median of the plotted points, to characterize the plot for subsequent analysis.

Once an indication of ordering is obtained at block 76, the indication is stored at a block 78. A look-up table constructed in similar fashion to that used in connection with block 62 is then consulted at block 80 to determine, for example, the microstructure, light scattering, and methods of diagnosis associated therewith. Finally, at block 82, each of these outputs is stored, along with the phase space plot and indication of ordering. The subsequent operation of processor 24 is then performed in accordance with the output routine 44 described above.

Figure 41:
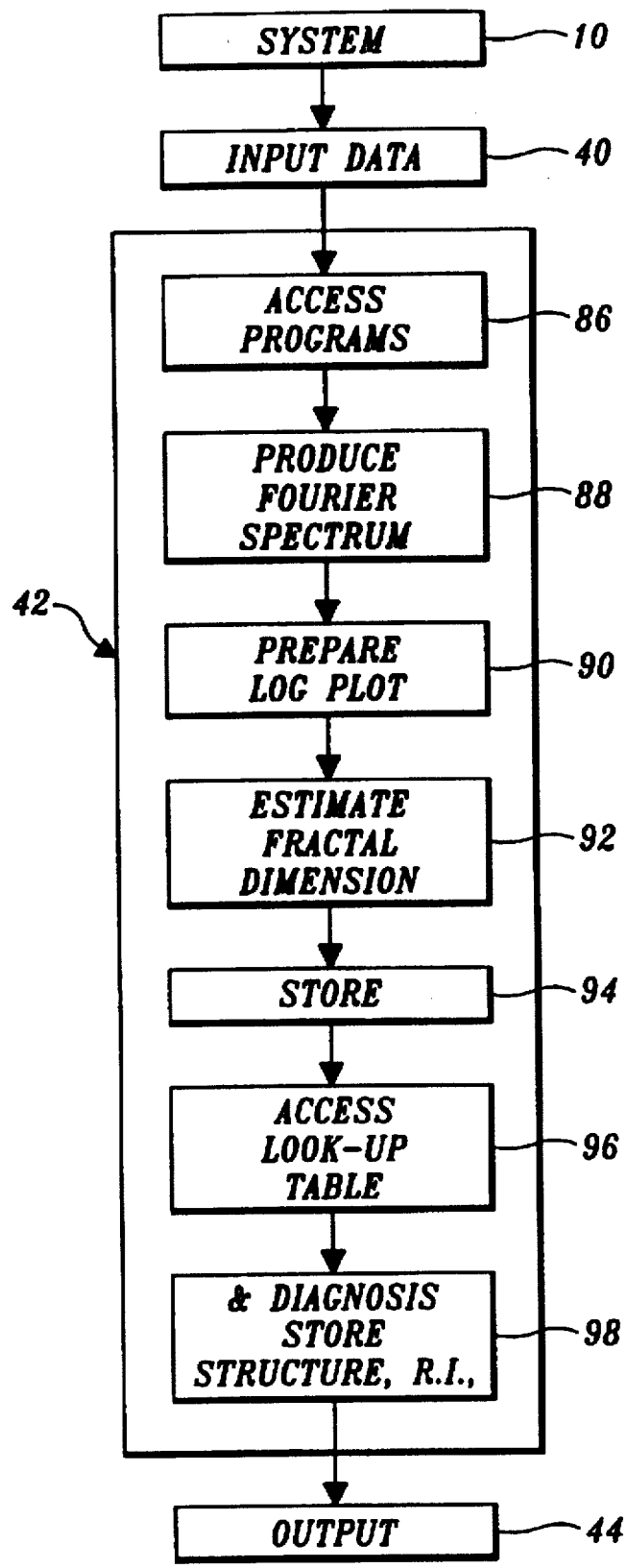
FIG. 41 is a flow chart illustrating another alternative to the analysis routine depicted in the flow chart of FIG. 11.
Figure 42:
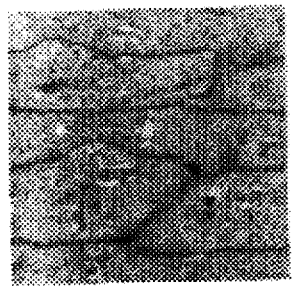
FIGS. 42-46 are a series of electron micrographs taken of a cataractus lens tissue growing more opaque from its periphery to its center.
Figure 43:
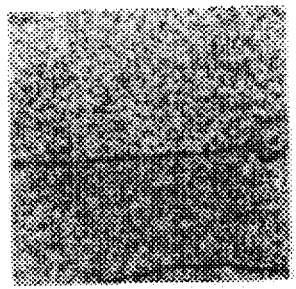
Figure 44:
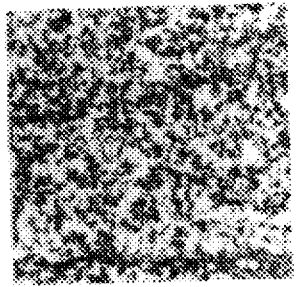
Figure 47:
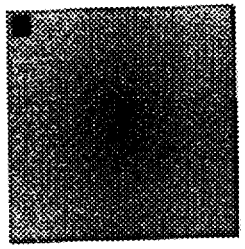
FIGS. 47-51 are the two-dimensional Fourier spectra associated with the FIGS. 42-46.
Figure 48:
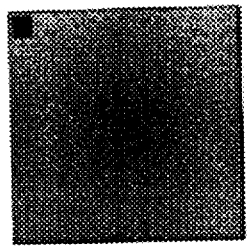
Figure 49:
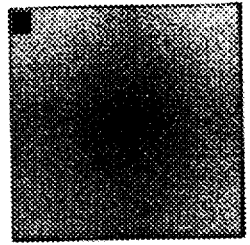
Figure 45:
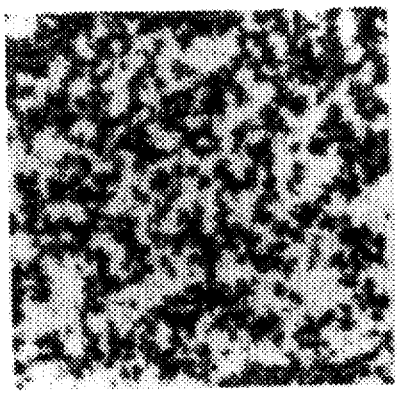
Figure 46:
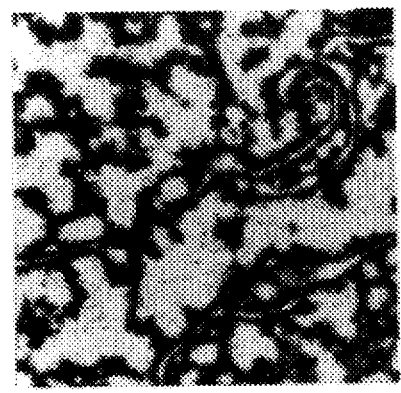
Figure 50:
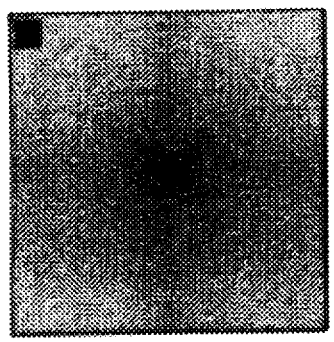
Figure 51:
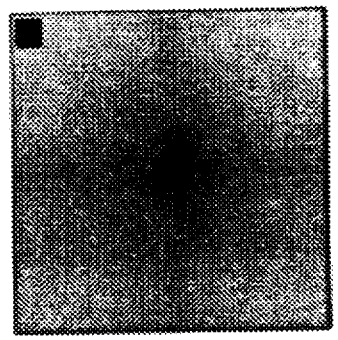
Figure 54:
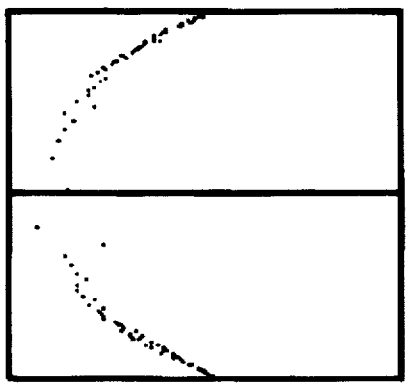
Figure 53:
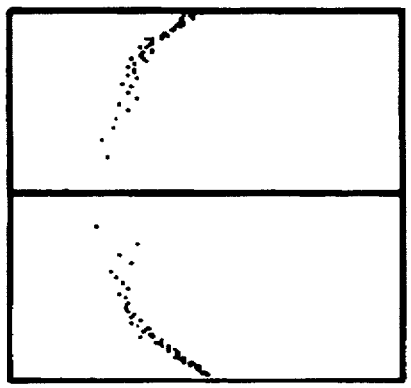
Figure 52:
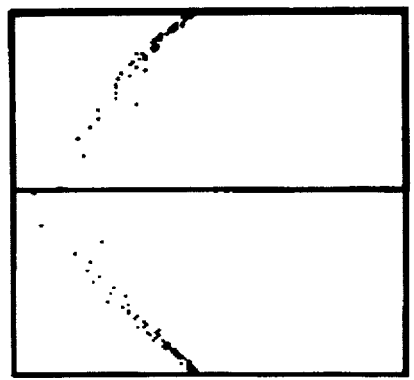
Figure 56:
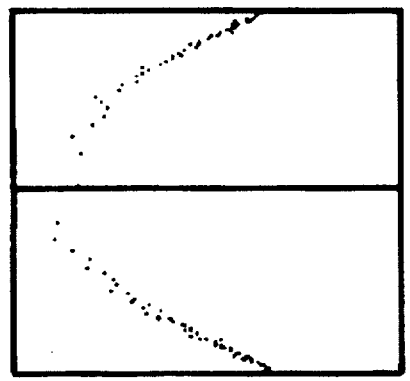
Figure 55:
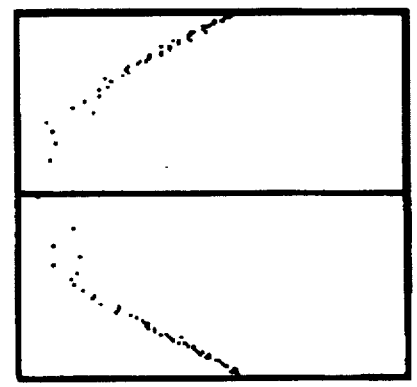

In addition to the fractal and oscillatory analyses illustrated in connection with FIGS. 23 and 28, another alternative processing technique has been developed employing a quantitative Fourier analysis to determine a fractal dimension used in the evaluation of any type of tissue sample, rather than to form the basis of a statistical analysis as in the prior art Fourier techniques described above. This analysis routine is shown in FIG. 41 and briefly includes the following steps.

First, at a block 86, the software routines required to provide the quantitative Fourier analysis and fractal analysis of the electron micrographs shown in FIGS. 42–46 are accessed. Next, at block 88, the one-dimensional Fourier spectrum associated with a line scans and two-dimensional Fourier spectrum associated with the images are computed. The two-dimensional Fourier spectra associated with the images are shown in FIGS. 47–51. A log-log plot of the amplitude of the Fourier components versus their frequency is prepared at block 90, followed by an estimation of the fractal dimension D of the two-dimensional spectrum based upon the slope of the log plot at block 92. The corresponding log-log plots are shown in FIGS. 52–56. This fractal dimension D is the corresponding equivalent to the fractal dimension D produced by the fractal analysis and is therefore also a function of the exponent $\beta$ of the power law function. Consequently, it is also indicative of the organization of the microstructure. The remaining steps of storage, comparison, and storage represented at blocks 94, 96, and 98, correspond to those discussed in connection with blocks 62, 64, and 66, discussed above.

In the various embodiments discussed above, in which program instructions are used to control the signal processing performed by computer 14, a complete programmed system 10 could be provided to the end user. Alternatively, data storage devices such as floppy disks including the program instructions could be provided to end users having the basic hardware components of system 10. Printed instruction manuals would be included with the floppy disks reviewing the operations performed by the software and the preprocessing and postprocessing operations to be performed by the operator. For example, guidelines might be provided regarding the manner of input data collection and preparation.

As previously noted, the recognition of the application of the power law function to normal and pathological microstructure is important to the application of the various signal processing techniques employed above. By employing these techniques, the system is able to resolve structural changes associated with relatively modest increases in pathology in any type of microstructure, providing a significant advance over the conventional one-dimensional, statistical-based Fourier analysis described above.

Figure 57:
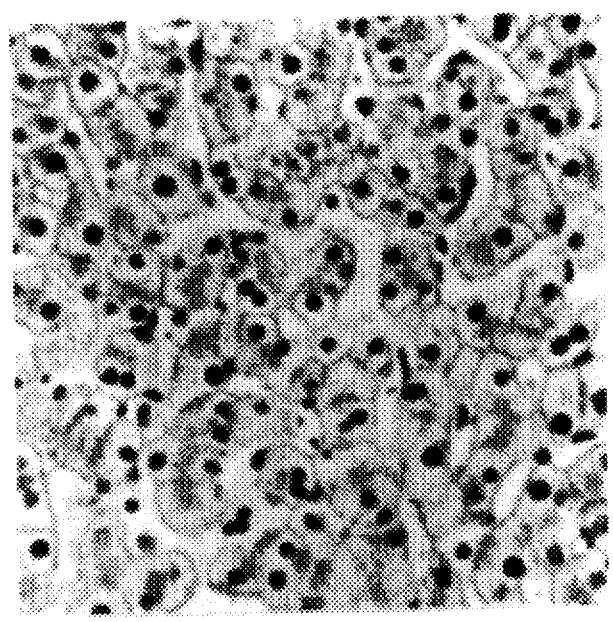
FIG. 57 is an electron micrograph taken of a normal liver tissue.
Figure 58:
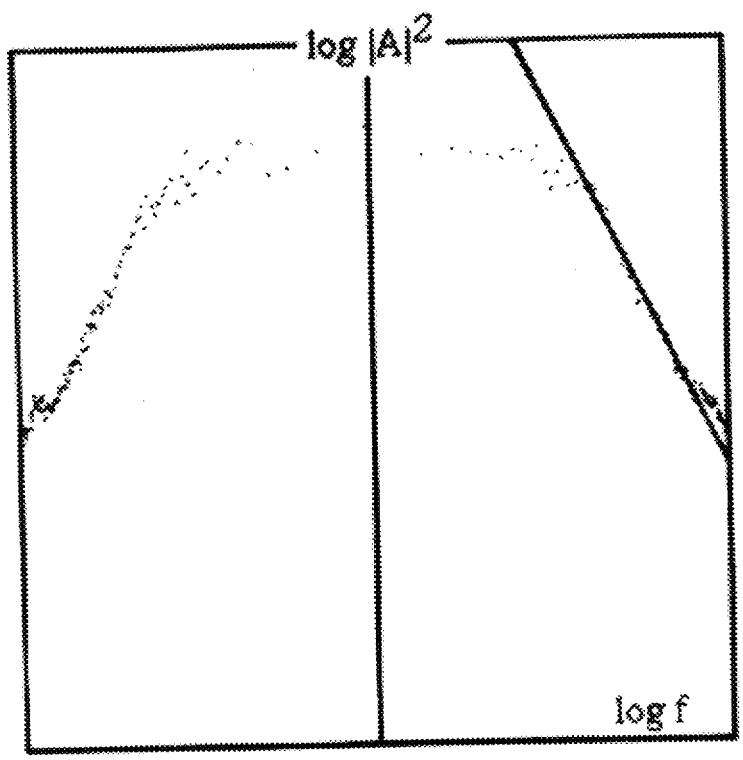
FIG. 58 is a log-log plot associated with the normal liver tissue.
Figure 59:
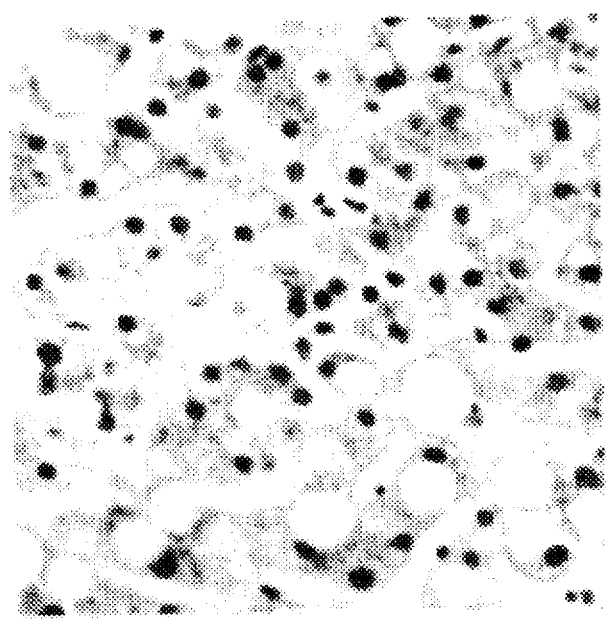
FIG. 59 is an electron micrograph taken of a diseased liver tissue.
Figure 60:
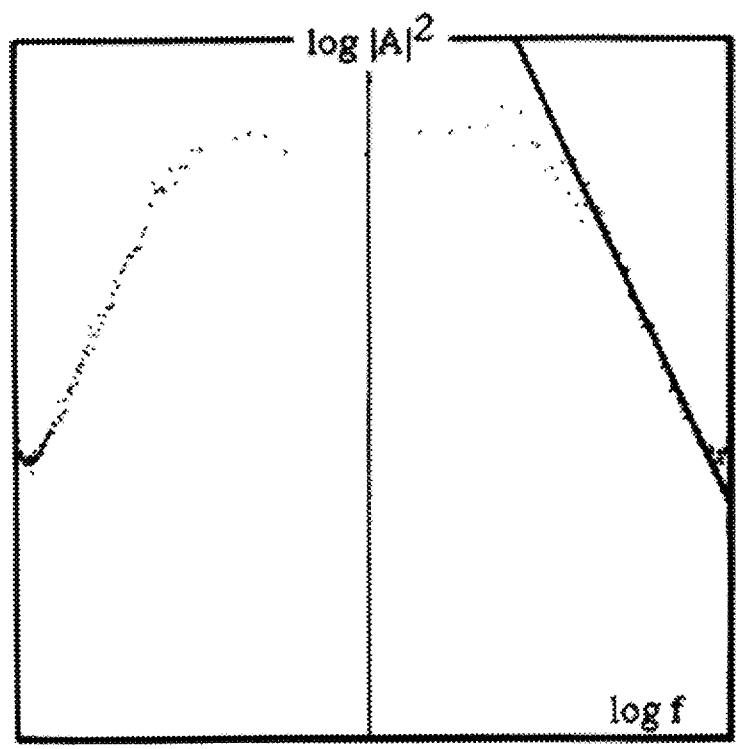
FIG. 60 is a log-log plot associated with the diseased liver tissue.

While the preferred embodiment of the invention has been illustrated and described, it will be appreciated that various changes can be made therein without departing from the spirit and scope of the invention. For example, as mentioned previously, the system has utility in a broad range of alternative applications including the detection and the development of methods for diagnosing of cataracts, cancer including leukemia, prostate and breast cancers, wound healing, skin diseases and diabetes, the automated analysis of pap smears, and the evaluation of trauma and aging. For example, electron micrographs of normal and diseased liver tissue appear in FIGS. 57 and 59. Their corresponding log-log plots depicting fractal dimension D are shown in FIGS. 58 and 60. A fractal dimension D of –0.48 is associated with normal liver tissue while a fractal dimension D of –0.54 is associated with diseased liver tissue. In addition, a variety of software algorithms can be used to evaluate the fractal dimension and determine the ordering of the phase space plot. For example, in addition to the techniques described above, a correlation dimension of the spatial density fluctuation can be computed, or a relative dispersion analysis can be used to evaluate the fractal dimension or determine the ordering associated with the phase space plot. In addition, a variety of alternative system constructions are contemplated including the use of hardware rather than software to perform the signal processing.

In accordance with another alternative, two or more of the signal processing techniques discussed above could be employed by the same system to allow several independent assessments of microstructure to be obtained. This multilevel approach would then allow an averaged assessment of microstructure to be produced. Further, by comparing the results obtained using one technique with results obtained using another technique, potentially erroneous results can be identified and either discarded or flagged as such for further interpretation by the attending medical personnel.

As a related point, the system could be programmed for selective use in any one of a number of different applications. Memory 26 would then include, for example, separate files of clinical data associated with each of the different types of pathology, trauma, or aging to be evaluated. The operator would be required to input information regarding the nature of the condition to be evaluated, identifying the appropriate files to be used in subsequent processing of data characterizing the microstructure under evaluation.

The embodiments of the invention in which an exclusive property or privilege is claimed are defined as follows:

1. A system for evaluating a status of microstructure of cells and tissue, said system comprising:
    data input means for producing a data output graphically representing the microstructure;
    processing means for converting the data output into a quantitative diagnostic output indicative of the status of the microstructure using a technique employing a representation of a nonrandom nature of the microstructure as a power law function.

2. The system of claim 1, wherein said data input means comprises means for converting previously collected information into a data output suitable for use by the processing means.

3. The system of claim 1, wherein the data input means comprises data collection means, said data collection means being used for examining the microstructure in order to produce the data output.

4. The system of claim 3, wherein the data collection means comprises an electron microscope.

5. The system of claim 3, wherein the data collection means comprises a magnetic resonance imaging system.

6. The system of claim 3, wherein the dam collection means comprises a nuclear magnetic resonance spectrometer.

7. The system of claim 1, wherein the processing means comprises a computer programmed to perform said technique as part of the conversion of the data output to the diagnostic output.

8. The system of claim 7, wherein said technique is an oscillatory analysis conducted upon the data output.

9. The system of claim 7, wherein said technique is used to convert data output representative of the microstructure of ocular tissue into the diagnostic output, and wherein the diagnostic output is indicative of the degree of light scattering caused by degeneration of the microstructure and, hence, the extent of cataracts in the tissue.

10. The system of claim 7, wherein said technique is used to convert data output representative of the microstructure of tissue into the diagnostic output, and wherein the diagnostic output is indicative of the degree of structural degeneration of the microstructure and the presence of cancer.

11. The system of claim 7, wherein said technique is a fractal analysis conducted upon the data output.

12. A system for evaluating a status of microstructure of cells and tissue, the system comprising:
   data input means for producing a data output representing the microstructure;
   processing means for converting the data output into a quantitative diagnostic output indicative of the status of the microstructure using a technique employing a representation of a nonrandom nature of the microstructure as a power law function, wherein said processing means comprises a computer programmed to perform said technique as part of the conversion of the data output to the quantitative diagnostic output, and wherein said technique is a fractal analysis conducted upon the data output.

13. The system of claim 12, wherein said fractal analysis employs a box-counting technique.

14. The system of claim 13, wherein said technique used for converting data output into the diagnostic output is a one-dimensional fractal analysis.

15. The system of claim 13, wherein said technique used for converting data output into the diagnostic output is a multi-dimensional fractal analysis.

16. The system of claim 12, wherein the power law function can be expressed by the equation:

$$|A|^2 = (1/f)^\beta$$

wherein A is an amplitude of a Fourier component associated with the data output, f is a frequency of a Fourier component associated with the data output, and $\beta$ is an exponent of the power law function.

17. The system of claim 16, wherein said technique converts the data output into a diagnostic output equivalent to fractal dimension D, and wherein fractal dimension D is a function of the exponent $\beta$ of the power law function.

18. The system of claim 17, wherein said technique is used to convert data output representative of ocular tissue into the diagnostic output equivalent to fractal dimension D, and wherein the fractal dimension D is indicative of the degree of light scattering caused by the degeneration of the microstructure and, hence, the extent of cataracts in the tissue.

19. The system of claim 18, wherein said fractal dimension D indicating cataracts in ocular tissue is within a range of fractal dimensions known to indicate the presence of cataracts.

20. A method of evaluating a status of microstructure of cells and tissue, the method comprising:
   producing a data output graphically representing the microstructure; and
   processing the data output to produce the quantified output indicative of the state of the microstructure using a characterization of the nonrandom nature of the data output as a power law function.

21. The system of claim 20, wherein processing the data output further characterized by expressing the power law function by the equation:

$$|A|^2 = (1/f)^\beta$$

wherein A is an amplitude of a Fourier component associated with the data output, f is a frequency of a Fourier component associated with the data output, and $\beta$ is an exponent of the power law function.

22. The method of claim 20, wherein processing the data output comprises:
   performing an oscillatory analysis of the data output to produce a phase space plot associated with the data output; and
   converting the phase space plot into the quantified output.

23. The method of claim 20, wherein processing the data output comprises performing a fractal analysis of the data output to produce quantified output.

24. A method of evaluating a status of microstructure of cells and tissue, the method comprising:
   producing a data output graphically representing the microstructure; and
   processing the data output to produce the quantified output indicative of the state of :the microstructure using a characterization of the nonrandom nature of the data output as a power law function, wherein processing the data output comprises:
   expressing the power law function by the equation:

$$|A|^2 = (1/f)^\beta$$

wherein A is an amplitude of a Fourier component associated with the data output, f is a frequency of a Fourier component associated with the data output, and $\beta$ is an exponent of the power law function; and
   performing a fractal analysis of the data output to produce a fractal dimension D as the quantified output, wherein the fractal dimension D is a function of the exponent $\beta$.

25. The method of claim 24, wherein processing the data output comprises:
   performing a Fourier analysis of the data output to produce a Fourier spectrum associated with the data output; and
   analyzing the Fourier spectrum to produce a fractal dimension D as the quantified output, wherein the fractal dimension D is a function of the exponent $\beta$.

26. The method of claim 24, wherein performing a fractal analysis of the data output comprises performing a box-counting technique.

27. The method of claim 26, wherein performing a fractal analysis comprises performing a one-dimensional fractal analysis.

28. The method of claim 26, wherein performing a fractal analysis comprises performing a multi-dimensional fractal analysis.

29. A system for assessing the microstructure of cell and tissue samples, said system comprising:
   an electron microscope for producing an output graphically representing the microstructure;
   a processor which processes the output of the electron microscope using a characterization of the nonrandom nature of the electron microscope output as a power law function, to produce an indication associated with the microstructure and for evaluating that indication to produce a system-output representative of the microstructure.

30. The system of claim 29, wherein the tissue sample is ocular tissue and wherein the system output produced by the processing means is representative of the degree of light scattering exhibited by the ocular tissue.

31. The system of claim 29, wherein the processor processes the output of the electron microscope by performing a fractal analysis on the output to produce the system output representative of the microstructure.

32. The system of claim 29, wherein the power law function is expressed by the equation:

$$|A|^2 = (1/f)^\beta$$

wherein A is an amplitude of a Fourier component associated with the data output, f is a frequency of a Fourier component associated with the data output, and $\beta$ is an exponent of the power law function.

33. The system of claim 32, wherein the processor processes the output of the electron microscope by performing a Fourier analysis on the output to produce a fractal dimension D as the indication associated with the microstructure, and wherein fractal dimension D is a function of exponent $\beta$.

34. The system of claim 29, wherein the processor processes the output of the electron microscope by performing an oscillatory analysis on the output to produce a phase space plot as the indication associated with the microstructure.

35. The system of claim 34, wherein the processor evaluates the phase space plot by extracting information from the plot that is then compared to information extracted from phase space plots associated with known microstructures.

36. A system for assessing the microstructure of cell and tissue samples, said system comprising:

an electron microscope for producing an output graphically representing the microstructure;

a processor for processing the output of the electron microscope using a characterization the nonrandom nature of the electron microscope output as a power law function to produce indication associated with the microstructure and for evaluating that indication to produce a system output representative of the microstructure, wherein the power law function is expressed by the equation:

$$|A|^2 = (1/f)^\beta$$

wherein A is an amplitude of a Fourier component associated with the data output, f is a frequency of a Fourier component associated with the data output, and $\beta$ is an exponent of the power law function; and wherein the processor processes the output of the electron microscope by performing a fractal analysis on the output to compute a fractal dimension D as the indication associated with the microstructure, and wherein the fractal dimension D is a function of exponent $\beta$.

37. The system of claim 36, wherein the processor evaluates the fractal dimension D by comparing the fractal dimension D to a range of fractal dimensions associated with known microstructures.

38. A system for assessing the microstructure of cell and tissue samples, said system comprising:

an electron microscope for producing an output graphically representing the microstructure;

a processor for processing the output of the electron microscope using a characterization of the nonrandom nature of the electron microscope output as a power law function, to produce an indication associated with the microstructure and for evaluating that indication to produce a system output representative of the microstructure, wherein the power law function is expressed by the equation:

$$|A|^2 = (1/f)^\beta$$

wherein A is an amplitude of a Fourier component associated with the data output, f is a frequency of a Fourier component associated with the data output and $\beta$ is an exponent of the power law function; and wherein the processor processes the output of the electron microscope by performing a Fourier analysis on the output to produce a fractal dimension D as the indication associated with the microstructure, and wherein fractal dimension D is a function of exponent $\beta$.

39. The system of claim 38, wherein the processor evaluates the fractal dimension D by comparing the fractal dimension D to a range of fractal dimensions associated with known microstinctures.

40. A system for evaluating a status of microstructure of cells and tissue, said system comprising:

data input means for producing a data output graphically representing the nonrandom nature of the microstructure; and processing means for converting the data output into a diagnostic output indicative of the status of the microstructure using a fractal analysis which converts the data output into the diagnostic output.

41. The system of claim 40, wherein said fractal analysis employs a box-counting technique.

42. The system of claim 41, wherein said fractal analysis used for converting data output into the diagnostic output is a one-dimensional fractal analysis.

43. The system of claim 41, wherein said fractal analysis used for converting data output into the diagnostic output is a multi-dimensional fractal analysis.

44. A system for evaluating a status of microstructure of cells and tissue, said system comprising:

data input means for producing a data output graphically representing the nonrandom nature of the microstructure; and processing means for converting the data output into a diagnostic output indicative of the status of the microstructure using an oscillatory analysis to produce a phase space plot as the diagnostic output.

45. A system for evaluating a status of structure, said system comprising:

data input means for producing a data output representing characterizing the nonrandom nature of the structure; and processing means for converting the data output into a quantitative output indicative of the status of the structure using a technique employing a representation of a nonrandom nature of the structure as a power law function.

46. The system of claim 45, wherein said technique is a fractal analysis conducted upon the data output.

47. The system of claim 45, wherein said technique is an oscillatory analysis conducted upon the data output.

* * * * *

UNITED STATES PATENT AND TRADEMARK OFFICE
CERTIFICATE OF CORRECTION

PATENT NO. : 5,719,784
DATED : February 17, 1998
INVENTOR(S) : J.I. Clark et al.

Page 1 of 2

It is certified that error appears in the above-identified patent and that said Letters Patent is hereby corrected as shown below:

| COLUMN | LINE | |
|---|---|---|
| 14 (Claim 6, | 57 line 1) | "dam" should read --data-- |
| 16 (Claim 23, | 17 line 3) | After "produce" insert --the-- |
| 16 (Claim 24, | 24 line 6) | "state of :the" should read --state of the-- |
| 16 (Claim 29, | 66 line 10) | "system-output" should read --system output-- |
| 17 (Claim 36, | 39 line 6) | After "characterization" insert --of-- |
| 17 (Claim 36, | 41 line 8) | "function to produce indication" should read --function, to produce an indication-- |
| 18 (Claim 38, | 14 line 17) | After "output" insert --,-- |

UNITED STATES PATENT AND TRADEMARK OFFICE
CERTIFICATE OF CORRECTION

PATENT NO. : 5,719,784
DATED : February 17, 1998
INVENTOR(S) : J.I. Clark et al.

It is certified that error appears in the above-identified patent and that said Letters Patent is hereby corrected as shown below:

| COLUMN | LINE | |
|---|---|---|
| 18 (Claim 39, | 24 line 4) | "microstinctures." should read --microstructures.-- |

Signed and Sealed this

Fifth Day of May, 1998

Attest:

Attesting Officer

BRUCE LEHMAN

Commissioner of Patents and Trademarks